(12) United States Patent
Lawrence et al.

(10) Patent No.: US 10,060,887 B2
(45) Date of Patent: Aug. 28, 2018

(54) FIELD SAMPLING KIT AND METHODS FOR COLLECTING AND DETECTING ALKYL METHYLPHOSPHONIC ACIDS

(75) Inventors: Richard J. Lawrence, Fort Detrick, MD (US); J. Richard Smith, Fort Detrick, MD (US); Benedict R. Capacio, Fort Detrick, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/885,634

(22) PCT Filed: Nov. 15, 2011

(86) PCT No.: PCT/US2011/060780
§ 371 (c)(1),
(2), (4) Date: Dec. 26, 2013

(87) PCT Pub. No.: WO2012/138384
PCT Pub. Date: Oct. 11, 2012

(65) Prior Publication Data
US 2014/0113380 A1    Apr. 24, 2014

Related U.S. Application Data

(60) Provisional application No. 61/458,797, filed on Nov. 15, 2010.

(51) Int. Cl.
| | | |
|---|---|---|
| *G01N 30/02* | (2006.01) | |
| *B01J 20/281* | (2006.01) | |
| *G01N 1/10* | (2006.01) | |
| G01N 1/02 | (2006.01) | |
| G01N 1/00 | (2006.01) | |
| G01N 1/14 | (2006.01) | |
| G01N 1/28 | (2006.01) | |

(52) U.S. Cl.
CPC ............. *G01N 30/482* (2013.01); *G01N 1/10* (2013.01); *G01N 2001/005* (2013.01); *G01N 2001/022* (2013.01); *G01N 2001/149* (2013.01); *G01N 2001/2826* (2013.01); *Y10T 436/163333* (2015.01)

(58) Field of Classification Search
CPC ...... G01N 30/482; G01N 30/48; G01N 30/02; G01N 30/00
USPC ............................ 436/104, 103; 422/430, 50
See application file for complete search history.

(56) References Cited

U.S. PATENT DOCUMENTS

| | | | | |
|---|---|---|---|---|
| 4,240,547 A | * | 12/1980 | Taylor .......................... | 206/204 |
| 6,403,329 B1 | * | 6/2002 | Novak et al. ................... | 435/20 |
| 2005/0059162 A1 | * | 3/2005 | Wohleb ......................... | 436/177 |

OTHER PUBLICATIONS

Richardson et al, Reverse phase ion-pairing HPLC-ICP-MS for analysis of organophosphorous chemical warfare agent degradation products, Journal of Analytical Atomic Spectrometry, 2006, 21, pp. 396-403. (Year: 2006).*
Driskell et al, Quantitation of Organophosphorus Nerve Agent Metabolites in Human Urine Using Isotope Dilution Gas Chromatography-Tandem Mass Spectrometry, Journal of Analytical Toxicology, Jan./Feb. 2002, 26, pp. 6-10 (Year: 2002).*
Mester et al, Trace element speciation using solid phase microextraction, Spectrochimica Acta Part B, 2005, 60, 1243-1269. (Year: 2005).*
Richardson, Douglas, et al., Ultra-Trace Analysis of Organophosphorous Chemical Warfare Agent Degradation Products by HPLC,-ICP-MS, Agilent Technologies, 2006, pp. 1-8. (Year: 2006).*

* cited by examiner

*Primary Examiner* — Christine T Mui
(74) *Attorney, Agent, or Firm* — Elizabeth Arwine, Esq.

(57) ABSTRACT

The invention relates to kits and methods of collecting and detecting alkyl methylphosphonic acids from environmental or biological liquids using a sorbent material. The sorbent material may be transported, desorbed and tested for alkyl methylphosphonic acids.

19 Claims, 5 Drawing Sheets

FIG. 1

| AMPA | R-group | (M-H)⁻ (amu) | Isotopic Label | IS (M-H)⁻ (amu) |
|---|---|---|---|---|
| \multicolumn{5}{c}{R-methyl phosphonic acid} | | | | |

R-methyl phosphonic acid

| AMPA | R-group | (M-H)⁻ (amu) | Isotopic Label | IS (M-H)⁻ (amu) |
|---|---|---|---|---|
| EMPA |  | 123 |  | 128 |
| IMPA |  | 137 |  | 140 |
| PMPA |  | 179 |  | 185 |
| CMPA |  | 177 |  | 183 |
| MMPA |  | 151 | | 155 |

FIELD SAMPLING KIT AND METHODS FOR COLLECTING AND DETECTING ALKYL METHYLPHOSPHONIC ACIDS

RELATED APPLICATIONS

This application is a national phase application under 35 USC § 371 of PCT Application No. PCT/US2011/060780, filed on Nov. 15, 2011 which claims the benefit of U.S. Provisional Patent Application No. 61/458,797, which was filed Nov. 15, 2010 and are incorporated by reference herein.

GOVERNMENTAL INTERESTS

The invention was made with government support. The government may have certain rights in the invention.

FIELD OF INVENTION

The invention relates to field kits and methods for collecting and detecting alkyl methylphosphonic acids from environmental or biological samples. The samples are generally contacted with a sorbent material and then transported to a separate location for analysis of sorbed analyte.

BACKGROUND

Exposure to chemical warfare agents (CWAs) continues to be a significant concern for both military and civilian populations. The potential for exposure to CWAs exists from multiple arenas including terrorist threats, demilitarization operations for the destruction of chemical stockpiles, and military battlefield contact.

Determination of whether an exposure to CWAs has occurred is of critical importance. In particular, determining the presence, identity, and level of exposure to organophosphonate nerve agents can be important in responding to an exposure. Organophosphonate nerve agents degrade into alkyl methylphosphonic acids which can be detected from liquid samples. Previous studies have shown alkyl methylphosphonic acids to be present in the urine of humans exposed to organophosphonate nerve agents. However, levels of alkyl methylphosphonic acids may diminish significantly over a relatively short time. Current methods of determining exposure to organophosphonate CWAs from the field involves shipping refrigerated liquid samples or freezing samples on dry ice to an analytical facility. Such methods are costly, require specialized packaging, and are not suitable to many types of transportation. Thus, sample collection techniques which preserve the sample for analysis and reduce the need for specialty packing are needed.

SUMMARY

The present invention provides a field kit for the collection and detection of alkyl methylphosphonic acids wherein the kit comprises a sorbent material which is capable of sorbing alkyl methylphosphonic acids. The kit further comprises a volumetric container, an acid, and one or more internal standard solutions. The kit may further comprise a specimen collection receptacle, a transportation container and/or and a mailer for shipping.

The present invention is further directed to methods of detecting alkyl methylphosphonic acids in liquid samples. The liquid samples may be environmental samples or biological samples. The method comprises collecting the liquid sample in a sorbent material. The sorbent material is capable of transporting the sorbed analyte to a facility for analysis, the analyte is then desorbed, and the desorbed analyte is tested for the presence of alkyl methylphosphonic acids.

The kit and method of the invention may provide an efficient way of determining the presence of alkyl methylphosphonic acids in locations where analytical capacities may be limited. The sorbed analyte in the fiber may be shipped or transported from one location to another without the need for specialized packaging. Further, the sorbent material may preserve the alkyl methylphosphonic acids until they can be analyzed. The samples may then be analyzed to determine the identity of the organophosphonate nerve agents, as well as the concentration of the sample, which may provide information as to the timing and severity of exposure.

Other aspects and iterations of the disclosure will be described in more detail below.

DETAILED DESCRIPTION

"Sorbed analyte" or "sorbed analytes" as used herein refers to the compounds present in the sample as held in the sorbent material.

"Desorption solution" as used herein refers to the solution formed by contacting the sorbed analyte with an extraction solvent.

"Desorption gas" refers to the gas produced when a sorbed analyte is thermally extracted from a sorbent material.

The present invention relates to kits and methods for the collection and detection of alkyl methylphosphonic acid chemical warfare degradation products. The kits and methods use sorbent materials to collect the chemical warfare degradation products from liquid samples. The kits facilitate transportation of the analyte of interest in the sorbent material from the field to a facility capable of analytically determining the presence, type and/or amount of alkyl methylphosphonic acid in the sample. The kits of the present invention generally comprise an acid, a sorbent material, a volumetric container, and one or more internal standard solutions. The kit may further comprise a transportation container, a specimen collection receptacle, and/or a mailer. The method generally comprises (a) collecting a sample; (b) contacting the sample with a sorbent material, (c) desorbing the analyte from the sorbent material; and (d) testing the desorbed analyte for the presence of alkyl methylphosphonic acids.

Organophosphonate nerve agents such as soman (GD) (O-Pinacolyl methylphosphonofluoridate), Russian VX (RVX) (N,N-diethyl-2-(methyl-(2-methylpropoxy)phosphoryl) sulfanylethanamine), cyclosarin (GF) (cyclohexyl methylphosphonofluoridate), sarin (GB) (isopropyl methylphosphonofluoridate), and VX (Ethyl({2-[bis(propan-2-yl) amino]ethyl}sulfanyl)(methyl)phosphinate)) are extremely toxic such that their primary application is as chemical warfare agents. Organophosphonate nerve agents degrade into alkyl methylphosphonic acids, which are comparatively safer to detect. Degradation products of organophosphonate nerve agents include pinacolyl methylphosphonic acid (PMPA), a degradation product of agent GD; 2-(methyl) propyl methylphosphonic acid (MMPA), a degradation product of agent RVX; cyclohexyl methylphosphonic acid (CMPA), the degradation product of agent GF; isopropyl methylphosphonic acid (IMPA), the degradation product of agent GB; and ethyl methylphosphonic acid (EMPA), the degradation product of agent VX. As used herein, "degradation product" may refer to a metabolite produced by introduction of the nerve agent to a living organism, or may refer to a non-physiological breakdown product.

I. Kits for Collecting a Chemical Warfare Degradation Product

One aspect of the invention is a kit that can be used in the field for the collection of a chemical warfare degradation product. Generally, the kit comprises an acid, a sorbent material, a volumetric container, and one or more internal standard solutions. The kit may further comprise a transportation container, a specimen collection receptacle, and/or a mailer. The kit is configured such that a liquid sample can be prepared in the field and shipped to a facility for analytical testing.

The kit comprises a sorbent material. The sorbent material in the kit is suitable to sorb a liquid including alkyl methylphosphonic acid degradation products and release the sorbed analytes such that they can be analyzed. In some aspects of the invention, the sorbent material is a solid phase microextraction fiber (SPME fiber). Examples of SPME fibers include polydimethylsiloxane (PDMS), poly-dimethylsiloxane/divinylbenzene (PDMS/DVB), carbowax/polyethylene glycol (CW/PEG), carbowax/templated resin (CW/TPR), octadecylsilyl ($C_{18}$), and polyacrylate (PA), and the like. In some aspects of the invention, the SPME fiber is commercially available. For example, octadecylsilyl ($C_{18}$) fibers may be those sold under as SPME-LC Fiber Probe, 45 um $C_{18}$ Silica Coating, RED Hub, product number 57281-U (Supelco, Bellefonte, Pa.). In preferred embodiments, the sorbent material is a carbowax-templated resin (CW/TPR) fibers or ($C_{18}$) fibers.

The amount of fiber present in the kit depends on the thickness and the amount and concentration of sample to be sorbed. Preferably, enough fiber is present to sorb about the analytes in detectable levels. In some aspects the thickness of the fiber may range between about 25 μm and about 250 μm. In other aspects, the thickness of the fiber may range between about 50 μm and about 100 μm. In yet another embodiment, the fiber thickness may range between about 75 μm and about 100 μm. Preferably, the fiber thickness is about 100 μm. In some embodiments, the surface area of the fiber may range between about 1 $mm^2$ and 1 $cm^2$, or in another embodiment between about 5 $mm^2$ and 15 $mm^2$.

Suitable sorbent materials may be present in the kit in various configurations including strips, sleeves, rods, or coatings. In some aspects, the sorbent material may be physically attached to another component of the kit. For example, the sorbent material may be a coating in the volumetric container. In another embodiment, the sorbent material may be attached to the cap of the volumetric container. In yet another embodiment, the sorbent material is present in the kit as a retractable fiber assembly. For example, the retractable fiber assembly may be a SPME Fast Fit Fiber Assembly (Sigma Aldrich).

The kit further comprises a volumetric container. The volumetric container may be any container (i.e., a cup, vial, etc.) suitable for holding a liquid sample. The volumetric container may optionally contain volumetric measurements which may be useful in measuring out a desirable amount of the sample or other reagents. The volumetric container may be made of any material so long as the material is stable in the presence of an acid. Suitable materials include plastics, aluminum, stainless steel, and the like. The internal volume of the volumetric container depends on the size of the sorbent material and is preferably less than about 10 mL. In other embodiments, the internal volume of the volumetric container ranges from about 1 mL to about 5 mL. In a preferred embodiment, the internal volume of the volumetric container is about 3 mL. In some aspects, the volumetric container comprises a body and a cap. In some embodiments, the sorbent material may be attached to the cap. In other embodiments, the sorbent material may be coated on the internal volume of the body of the volumetric container.

In some embodiments, the volumetric container may additionally be configured for the type of sample collection contemplated and used for collection of the specimen, in other aspects a specimen collection receptacle is separately provided in the kit, and may be in the form of a cup, vial, pipette, or capillary tube.

The kit further comprises an acid for adjustment of the pH of the sample. Without being bound to any theory, it is thought that the acid may serve to maximize the transfer of the alkyl methylphosphonic acids to the sorbent material. The acid may be any known in the art. Generally the acid has a pKa lower than about 5. Suitable acids include, but are not limited to, acetic acid, formic acid, methane sulfonic acid, phosphoric acid, sulfuric acid, hydrochloric acid, hydrobromic acid, hydroiodic acid, trifluoromethane sulfonic acid, toluenesulfonic acid, and the like. Preferably, the acid is hydrochloric acid. The acid may be pre-mixed with water, salts or buffer solutions. The acid or the mixture of acid with water, salts or buffers may be provided in a liquid packet, in one or more capsules (such as for example in a flame sealed vial), and/or in another aspect component either sealed within a component of the kit or impregnated into the kit.

The amount of acid in the kit will depend on the type of sample that the kit is designed for (i.e. environmental water sample or biological fluid sample) as well as the size of the sample. Generally, the amount of acid acidic in the kit is sufficient to adjust the pH of the sample to below about 3. In some aspects, the pH of the sample is adjusted to about 2.5, or about 2, or about 1.5. The total volume of the acid in the kit may vary depending on the molarity and the size of the sample. In various aspects the amount of acid will vary between 50 µL and 3 mL, or between 75 µL and 1 mL, or more preferably between 100 µL and 300 µL.

Figure 1:
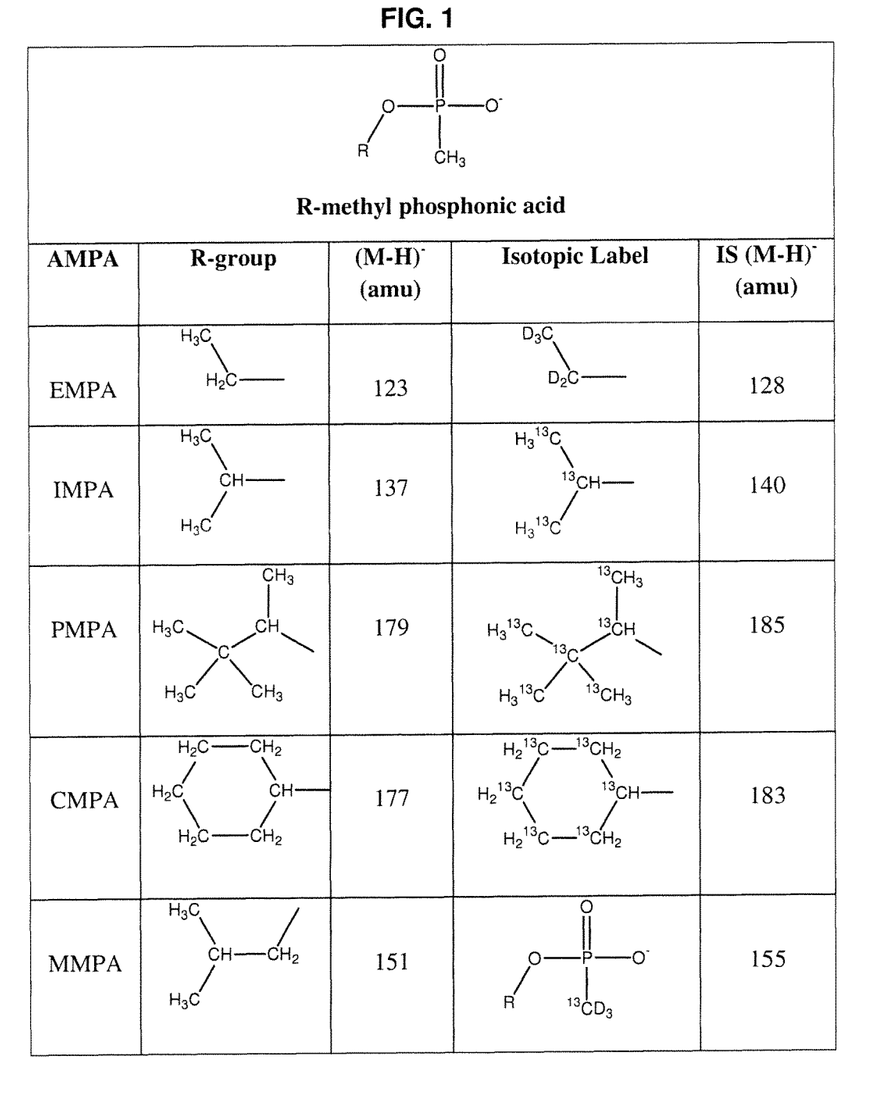
FIG. 1 shows the chemical structure of alkyl methylphosphonic acids and various degradation products as well as exemplary isotopically labeled degradation products and their expected masses for analysis by mass spectrometry.

The kit additionally comprises one or more internal standard solutions. In one embodiment, the kit contains an internal standard solution of isotopically labeled alkyl methylphosphonic acids. For example, the internal standard solution of the isotopically labeled alkyl methylphosphonic acid may be selected from the group consisting of EMPA, IMPA, PMPA, CMPA, MMPA, and combinations thereof. The isotopic label may be present at any position in the structure of the alkyl methylphosphonic acids, but preferably is present in the alkyl moiety. For example, the isotopically labeled alkyl methylphosphonic acids may be EMPA, ethyl-$D_5$; IMPA, isopropyl-$^{13}C_3$; PMPA, trimethylpropyl-$^{13}C_6$; CMPA, cyclohexyl-$^{13}C_6$; and MMPA, methylphosphonyl-$^{13}C$, $D_3$. Structures of these isotopically labeled metabolites are set forth in FIG. 1. Isotopically labeled alkyl methylphosphonic acids may be synthesized or obtained commercially, for example from Cerrilliant (Round Rock, Tex.).

In a preferred embodiment, the internal standard solution may comprise isotopically labeled EMPA, IMPA, PMPA, CMPA, MMPA in known amounts, such that a calibration curve can be made. In some embodiments, the isotopically labeled standards are dissolved in water, in other embodiments the isotopically labeled standards are dissolved in a synthetic biological solution, such as, for example synthetic urine. The total volume of the internal standard may vary depending on the size of the sample. The concentrations of the isotopically labeled alkyl methylphosphonic acids in the standard solution may vary. In some aspects, the concentration of one or more alkyl methylphosphonic acids may range from about 100 ng/mL to about 1 µL/ml. In some embodiments, the alkyl methylphosphonic acids are present in a concentration of about 500 ng/mL. In various aspects the total volume of the internal standard in the kit may be between 50 µL and 3 mL, or between 75 µL and 1 mL, or more preferably between 200 µL and 600 µL.

The kit may optionally comprise a transportation container. The transportation container may be any structure suitable for transportation of a sorbent material after it has been exposed to the liquid sample. The container is configured such that the sorbent material can be packed into the container and sealed to prevent wicking or contamination of the sorbent material. The container may be made of any material so long as the material is stable in the presence of an acid or a sample mixed with acid over the period of that the sorbent material will be in the transportation container. In some embodiments, the container is capable of storing the sorbent material over long periods of time. Suitable materials include plastics, aluminum, stainless steel, and the like. The internal volume of the transportation container depends on the size of the sorbent material and is preferably less than about 10 mL. In other embodiments, the internal volume of the transportation container ranges from about 1 mL to about 5 mL. In a preferred embodiment, the internal volume of the transportation container is about 3 mL. The transportation container may be, for example, a polypropylene centrifuge tube.

The kit may further comprise a mailer suitable for shipping the sample within the sealable receptacle to a laboratory for analysis. The mailer may be in the form of a protective envelope (i.e., padded envelope), a mailing container (i.e., box or tube), or the like.

In some embodiments, the kit comprises a volumetric container, an acid, a sorbent material in the form of a retractable fiber, and an internal standard solution comprising EMPA, IMPA, PMPA, CMPA, MMPA, and combinations thereof.

In another embodiment, the sorbent material may be physically attached to the volumetric container. In such embodiments, the volumetric container comprises a body and a cap. Prior to filling the volumetric container with the sample and any other reagents, the cap is removed. The liquid sample, acid, and isotopically labeled internal standard are added to the body of the volumetric container, and the cap is then returned to the volumetric container such that the sorbent material is placed in contact with the liquid in the volumetric container. After the desired period of time, the liquid is removed, the cap is resealed, and the fiber is transported in the volumetric container to a facility for analysis.

In still another embodiment, the sorbent material may coat all or part of the internal volume of the body of the volumetric container. In this embodiment, each reagent is added to the volumetric container and allowed to incubate for a period of time. The liquid contents of the volumetric container are then discarded and the volumetric container is sealed and shipped to a suitable facility for analysis.

II. Method of Collecting and Detecting a Chemical Warfare Degradation Product

In yet another aspect of the present invention, a method for detecting chemical warfare degradation products in environmental or biological samples using the field kit of Section (I) is provided. The process generally comprises (a) collecting a sample; (b) contacting the sample with a sorbent material, (c) desorbing the sorbed analyte from the sorbent material; and (d) testing the desorbed analytes for the presence of alkyl methylphosphonic acid. The presence of alkyl methylphosphonic acids may be determined, for example by gas chromatography-mass spectrometry (GC/MS), or by liquid chromatography-tandem mass spectrometry (LC/MS/MS).

The sample may be collected by any means known in the art, generally collecting the sample is collected in the volumetric container or the specimen collection receptacle of the kit. The sample may be any liquid, especially liquids thought to be exposed to organophosphonate nerve agents. In some embodiments, the liquid is an environmental liquid, such as a sample from freshwater or saltwater sources, for example a stream or body of water. In other aspects, the sample is a biological fluid such as, for example, blood, urine, serum, or saliva. Biological samples may be obtained for a variety of subjects. For example, the subject may be a human or a veterinary subject. Non-limiting examples of suitable veterinary subjects include companion animals such as cats, dogs, rabbits, horses, and rodents such as gerbils; agricultural animals such as cows, cattle, pigs, goats, sheep, horses, deer, chickens and other fowl; zoo animals such as primates, elephants, zebras, large cats, bears, and the like; and research animals such as rabbits, sheep, pigs, dogs, primates, mice, rats and other rodents.

Any amount of the sample may be collected; however, it is preferable to contact the sorbent material with a relatively small amount. The sample may either be collected in this amount, for example, by using volumetric measurements on the volumetric container or specimen collection receptacle. In other aspects, the sample is measured into the volumetric container or specimen collection receptacle. In some embodiments, the amount of sample is about 0.1 mL to about 10 mL. In other embodiments, the amount of sample is between about 3 mL and about 8 mL. In a preferred embodiment, the amount of sample is measured to be about 5 mL.

The method further comprises mixing the sample with other components of the kit and contacting the mixed components with the sorbent material. The method generally comprises contacting the sample with the acid and the internal standard as provided in the kit. These are generally allowed to mix or incubate such that each component is dispersed evenly throughout the mixture. In some aspects, the components may be stirred or shaken.

The amount of sample contacted with the fiber is not critical to the invention. One or more fibers may be combined where a single fiber is not sufficient for testing. In some aspects, the amount of liquid contacted with the sorbent material ranges between about 0.1 mL and about 10 mL. In other embodiments, the amount of liquid contacted with the sorbent material is about 1 mL to about 5 mL. In preferred aspects, the amount of sample contacted with the sorbent material is about 3 mL.

Generally, there is no upper limit to the amount of time which the sorbent material may be contacted with the sample mixture. In preferred aspects, the sorbent material is contacted with the sample liquid for less than about 15 minutes. In some embodiments, the sorbent material is contacted with the sample liquid for about 1 minute to about 10 minutes. In another embodiment, the sorbent material is contacted with the sample liquid for about 1 minute to about 5 minutes. Preferably, the sorbent material is contacted with the sample liquid for about 5 minutes.

In some aspects, the sample mixture is added in excess above the amount that the sorbent material is able to sorb, in such cases it may be preferable to drain the excess liquid from the sorbent material before packaging the sorbent material. The sorbent material may be packaged by placing the sorbent material in the container, or in some aspects by sealing a sorbent material attached to the container. The sorbent material comprising the sorbed analytes may be packaged while wet or dry. In some aspects, the sorbed analytes are packaged in the volumetric container, in others the sorbed analytes are packaged in the transportation container.

The previous steps are generally conducted with the kit in the field, that is, a location remote from a facility capable of analyzing the sorbed analyte. The method further comprises transportation of the sorbed to a facility capable of analyzing the samples for the presence of alkyl methylphosphonic acids. The sorbed analyte may be transported by any means known. In some aspects, the container is transported via a carrier or a postal system.

The method may preserve the sorbed analytes over an extended period of time. In some aspects, alkyl methylphosphonic acids are stable as sorbed in the sorbent material for a period of time greater than 5 months. In other aspects, the alkyl methylphosphonic esters are stable as sorbed in the sorbent material for a period of time greater than 3 months.

The sorbed analytes may be analytically tested by first desorbing the analytes from the sorbent material. Desorption may occur thermally where the analyte is heated to produce a desorption gas comprising the analyte. More preferably, desorption may involve immersing a sorbent material into a solvent for a period of time. Generally, the solvent is water, an organic solvent, a buffered solution, or a mixture thereof. Non-limiting examples of organic solvents are acetonitrile, acetone, allyl alcohol, benzene, butyl acetate, chlorobenzene, chloroform, chloromethane, cyclohexane, cyclopentane, dichloroethane, diethyl ether, dimethyl sulfoxide (DMSO), dimethylformamide, dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran, tetrachloroethane, toluene, trichloroethane, xylene and combinations thereof. In a preferred embodiment, the solvent is acetonitrile. Suitable buffers, without limitation may include amine buffers, bicarbonate buffers, borate buffers, and carbonate buffers. Buffers may be provided with any acceptable counterion including, but not limited to lithium, sodium, potassium, calcium, magnesium, and the like. When one or more solvents are mixed, they may be provided in any amount without limitation. For example, the solvents may be provided in approximately a 50:50 ratio, a 75:25 ratio, an 80:20 ratio, or a 90:10 ratio. Desorption of the sorbed analyte in a solvent gives a desorption solution of analyte and the desorption solvent.

Generally, the presence of alkyl methylphosphonic acids in the desorption solution or gas may be determined by any means. For instance, the alkyl methylphosphonic acids may be detected spectrophotometrically, by nuclear magnetic resonance, chromatography, mass spectrometry, or any other method known in the art. The alkyl methylphosphonic acids may be detected in relatively low concentration samples. In some aspects, the method can detect alkyl methylphosphonic acids in a liquid when the original concentration of the alkyl methylphosphonic acids in the liquid sample was below 50 ng/mL. In various aspects, the method may detect alkyl methylphosphonic acids in a liquid sample when the concentration of the alkyl methylphosphonic acids in the original liquid sample ranged from about 1 ng/mL to 17 ng/mL.

In some embodiments, the presence of alkyl methylphosphonic acids is determined by GC/MS (Gas Chromatography-Mass Spectrometry). Detection by GC/MS may require derivatization prior to introduction into the GC/MS, for example as described in Mui Tiang Sng et. al. J. Chromatogr. A., 832:173-182 (1999), which is hereby incorporated by reference.

More preferably, the presence of alkyl methylphosphonic acids is determined by LC/MS/MS (Liquid Chromatography Tandem Mass Spectrometry). LC/MS/MS allows for separation by liquid chromatography prior to tandem mass spectrometry. Injection can be accomplished after desorption with a suitable solvent, and in some aspects through the use of a SPME/HPLC interface. A SPME/HPLC interface allows the mobile phase to contact the sorbent material to remove the sorbed analytes. Analytes can be desorbed dynamically through a moving stream of mobile phase, or statically by being soaked in the mobile phase for a period of time prior to injection. Generally, the mobile phase may be an organic, water, or buffered solution as described above.

In one embodiment the LC/MS/MS is an Applied Biosystems API-4000 with Agilent 1000 LC Stack Waters Atlantis® silica column (1.0 mm×50 nm which is run at a flow rate of about 200 µL/min flow rate, and the mobile phase is and 86:14 mixture of acetonitrile to 20 mM ammonium acetate. In some aspects, the LC/MS/MS is followed with a post column addition (PCA) solvent. The PCA solvent may be any organic solvent. In a preferred embodiment, the PCA solvent is ethyl acetate (EtOAc).

Comparison to the internal standards provides information on the agent or agents in the samples. The samples may also be then be quantified to provide useful information concerning the relative degree and/or time-frame of exposure.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, formulations, or methods of use of the invention, may be made without departing from the spirit and scope thereof.

EXAMPLES

Example 1. HPLC Analysis of Various Commercial Fibers with Internal Standards in Water A 50 ng/mL solution of the internal standards containing EMPA, IMPA, PMPA, CMPA, MMPA was prepared in HPLC grade water. Four SPME fibers were evaluated for selectivity with the internal sample solution. The fibers evaluated were 100 μm PDMS, 60 μm PDMS/DVB, 50 μm CW/TPR, and 85 μm PA. Each fiber was given a 5 minute adsorption time in 3 mL of the internal standard solution, followed immediately by dynamic injection (desorption into the flowing stream of mobile phase) using a Supelco® SPME/HPLC interface. Peaks were observed in accordance with all of the IS transitions and retention times. The CW/TPR fiber provided the most intense response, followed by the PDMS, the PDMS/DVB, and finally the PA fiber. The CW/TPR fiber also provided the most balanced response for all the acids investigated. The PDMS fiber provided peak area responses that were skewed towards the earlier eluting, more hydrophobic side-chained acids (PMPA, MMPA, and CMPA) suggesting that they exhibited greater partitioning into the hydrophobic PDMS phase. The PDMS/DVB response was similar to the PDMS but slightly less intense, and the PA fiber response was low.

Example 2. Preparation of Urine Samples

Urine samples (3 mL) were pipetted into an empty 4 mL septum top vial. The internal standard mix (300 μL) was then added along with approximately 70 μL (3 drops) of 3.0 N HCl and a micro stirbar. A SPME assembly was inserted into the vial and the fiber was exposed to the urine sample through direct immersion at a consistent depth. The total exposure time was monitored. Once the desired time was reached, the fiber was retracted and removed from the sample vial.

Example 3. HPLC Analysis of Urine Samples

Figure 2:
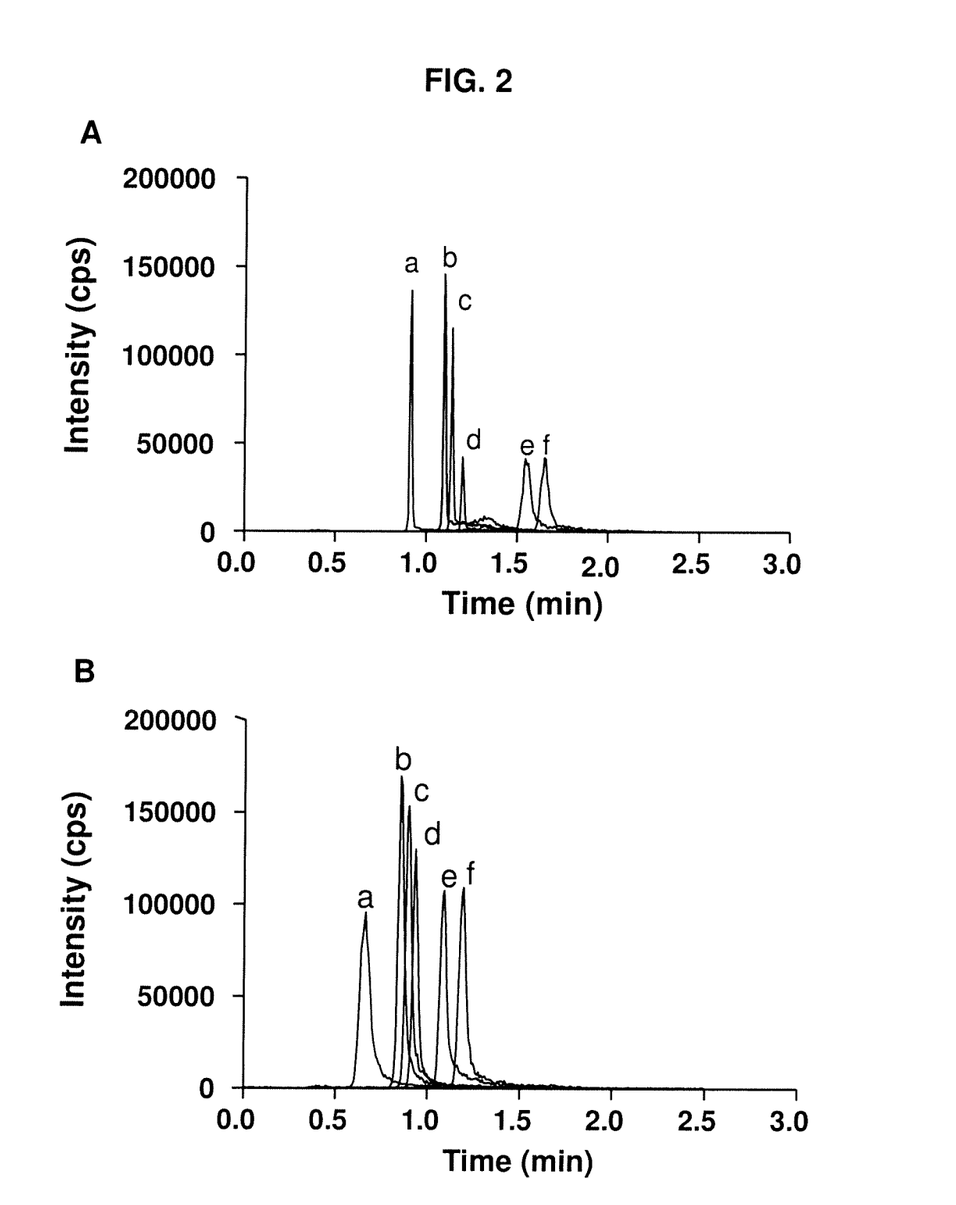
FIG. 2 is a reconstructed multiple reaction monitoring (MRM) chromatogram for EMPA-$D_5$ (A) and PMPA-$^{13}C_6$ (B) resulting from a 50 ng/mL internal standard mix in synthetic urine. Overlay of chromatograms obtained from six concentrations of water in acetonitrile: (a) 20%, (b) 15%, (c) 13%, (d) 10%, (e) 5%, and (f) 0%. Conditions: CW/TPR fiber, 5 minute adsorption, 1 minute equilibration in SPME HPLC interface, 2.1 mm Hydrophilic Interaction Liquid Chromatography (HILIC) column, mobile phase=86% acetonitrile/14% aqueous 20 mM ammonium acetate, and flow rate=500 µL/min.

Urine samples were treated with several drops of 3N HCl to adjust the pH to about 1.5 and contacted with CW/TPR. Preliminary experiments were conducted using the dynamic injection technique: the CW/TPR fiber was inserted into the SPME/HPLC interface (filled with a 15% water, 85% acetonitrile solution) and the valve was rotated to introduce a flowing stream of mobile phase. In order to establish control over the column loading, a CW/TPR fiber previously immersed in a 50 ng/mL standard synthetic urine sample was allowed to desorb for five minutes in 100 μL of mobile phase in a vial equipped with a glass insert. The fiber was removed; the vial was capped, and placed on an Agilent G1329A ALS HPLC auto sampler for injection. A 10 μL injection resulted in symmetrical peaks with resolution FIG. 2. The flow rate that should be used with the 1 mm column, by application of equation 3, is approximately 110 μL/min.

Figure 3:
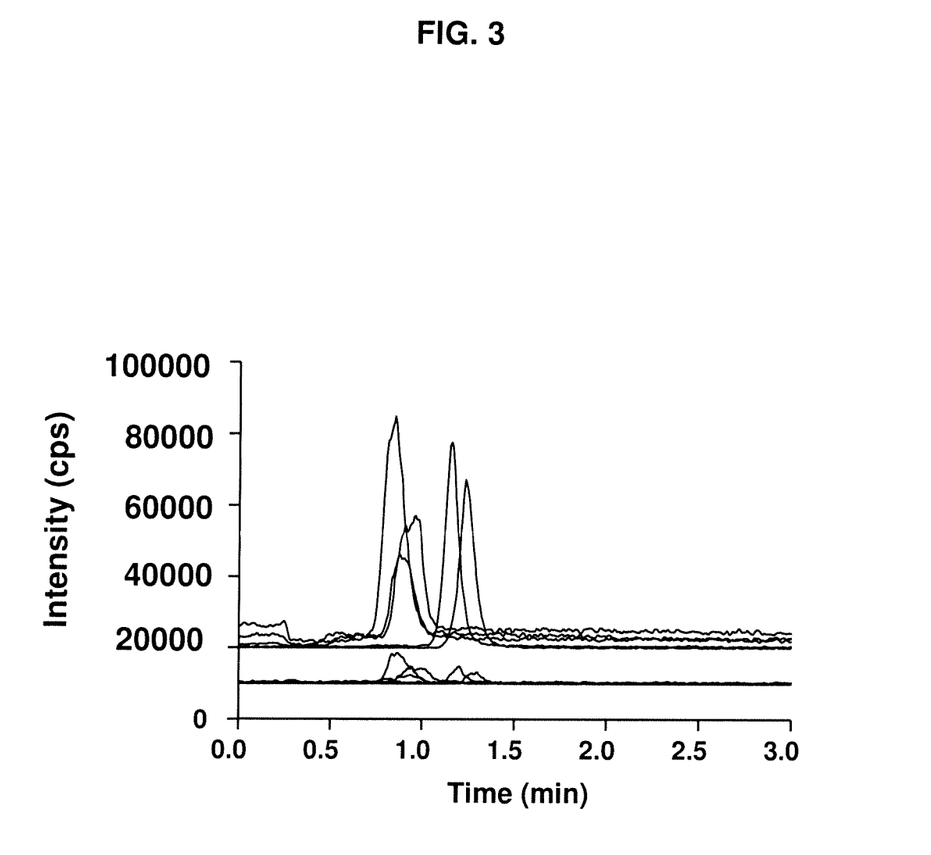
FIG. 3 is a reconstructed MRM chromatogram for five internal standards from a 50 ng/mL standard in synthetic urine. Elution order left to right: PMPA-$^{13}C_6$, MMPA-$^{13}CD_3$, CMPA-$^{13}C_6$, IMPA-$^{13}C_3$, and EMPA-$D_5$. The lower trace resulted from a 10 µL injection of standard solution with the post column addition (PCA) pump turned off. The upper trace shows the increase in sensitivity achieved from injection of the same standard solution incorporating PCA of ethyl acetate at 280 µL/min. The chromatograms were shifted 10,000 (lower trace) and 20,000 (upper trace) units along the ordinate for clarity.
Figure 4A:
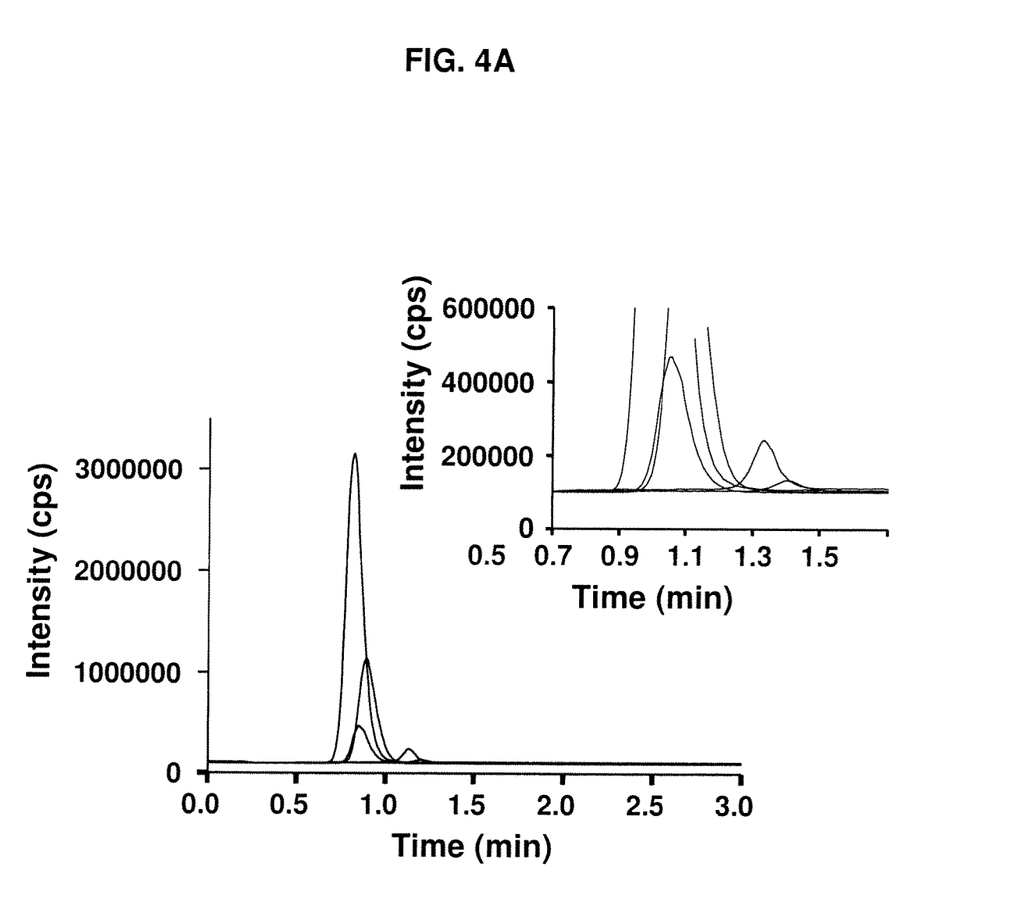
FIG. 4 are reconstructed MRM chromatograms for five analytes from a 100 ng/mL standard, comparison of ($C_{18}$) and CW/TPR fiber responses. The elution order left to right is PMPA, MMPA, CMPA, IMPA, and EMPA. (A) shows the response from ($C_{18}$) fiber, the insert is an expansion showing IMPA and EMPA peaks. (B) shows the response from CW/TPR fiber, the insert is an expansion showing IMPA and EMPA peaks. The chromatograms were shifted 100,000 units along the ordinate for clarity.
Figure 4B:
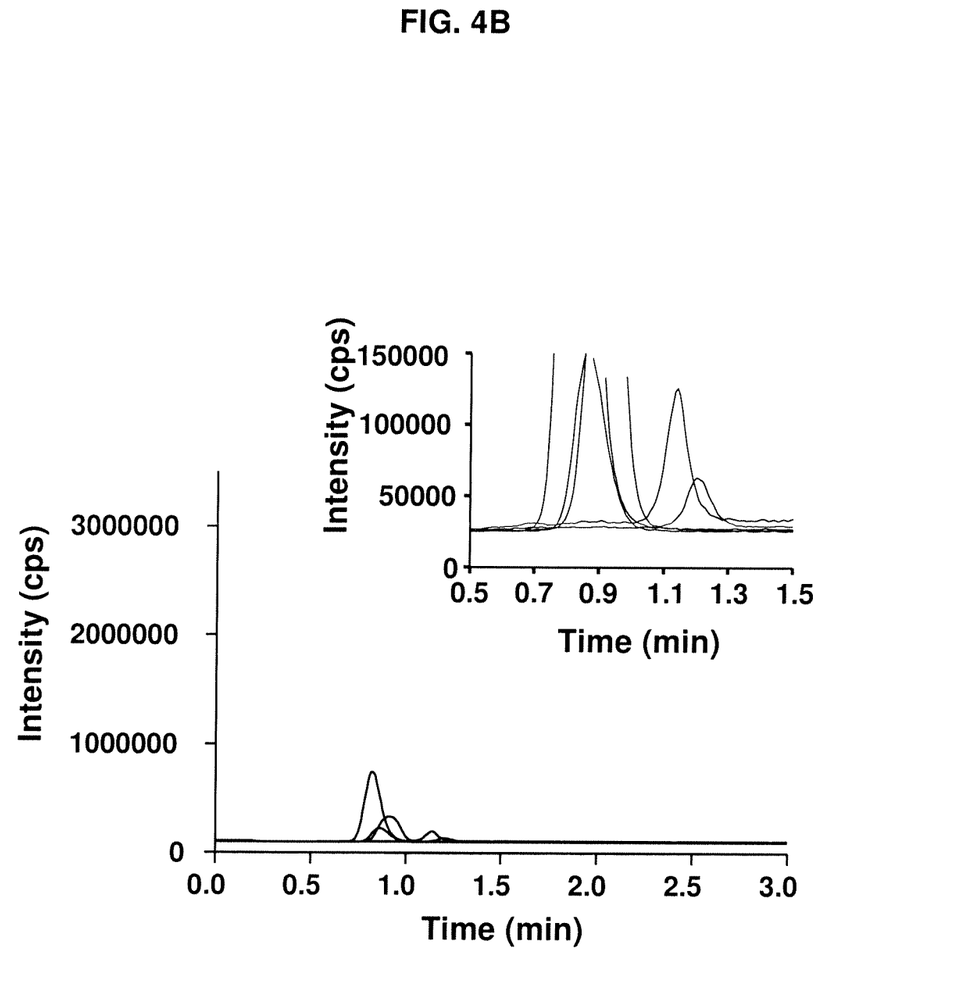

Example 4. LC/MS/MS Analysis of $C_{18}$ Fibers with Internal Standards in Water Octadecylsilyl ($C_{18}$) bonded phase fibers (Supelco) were evaluated. The $C_{18}$ fibers were evaluated against the CW/TPR fibers using the optimized method (1 mm column, 200 μL/min flow rate, 280 μL/min EtOAc PCA flow rate, 5 min. adsorption time, 5 minute desorption time in 100 uL of mobile phase, and 10 uL injection volume). Both fibers provided comparable responses for EMPA and IMPA; the ($C_{18}$) fiber provided a significant increase (approximately 3× the peak height) in response for the more hydrophobic side chained acids: PMPA, MMPA, and CMPA as shown in FIG. 3.

Example 5. Linearity and Limit of Detection, QC Samples Fiber Stability Study

Linearity of the quantitative method was verified for both the CW/TPR and ($C_{18}$) fibers for all five analytes. Utilizing the Cerilliant synthetic urine standards, an eight point curve (1, 2, 5, 10, 25, 50, 100, and 200 ng/mL) was constructed from the peak area ratio of the MRM transitions for each analyte over its corresponding internal standard as a function of the ratio of the standard concentration to IS concentration. In addition a mobile phase blank, method blank, and two QC samples (15 and 75 ng/mL) were also analyzed for each fiber (Table 1). Linearity was expressed as the correlation coefficient (R2) obtained from the linear regression analysis of the eight point curve with equal weighting. In all cases the R2 value exceeded 0.999 for both fibers.

The limit of detection was estimated by the signal to noise ratio (S/N) achieved for the lowest point (1 ng/mL) of the calibration curve. The S/N was calculated using the Analyst software. For both fibers, the EMPA S/N<10:1; however, the S/N for the 2 ng/mL standards exceeds 10:1 for both fibers. Likewise, the S/N calculated for IMPA at the 1 ng/mL level is approximately 10:1. Therefore the estimated limit of detection for these two analytes with the current method is EMPA=2 ng/mL and IMPA=1 ng/mL. The remainder of the analytes provided S/N greater than 10:1 for the lowest level standard and should be detectable in the high pg/mL range.

Along with the calibration curves, two QC samples were prepared and evaluated for each fiber as a means of verification. A low standard (QCL) supplied at 15 ng/mL and a high standard (QCH) supplied at 75 ng/mL were analyzed and the concentrations were calculated from the calibration curve (Table 1). The results obtained for the CW/TPR fiber indicate a positive bias for both QC samples. Those obtained for the $C_{18}$ fiber demonstrate the same positive bias, but to a lesser extent. The positive bias is believed to be due to carryover on the fiber from the previous run. The fibers used for the QCL and QCH samples were preceded by analysis of the 100 and 200 ng/mL standards, respectively. Injection of mobile phase blanks showed no evidence of carryover originating from the LC system.

The stability of the fibers was also tested in the same manner. The fibers were allowed a 5 minute adsorption period before retraction of the fiber into its sleeve and placement into a 15 mL polypropylene centrifuge tube. The tubes were stored at ambient temperature for 69 days prior to analysis. On the day of analysis, the fibers were desorbed into 100 µL of mobile phase for 5 minutes and analyzed in the same manner as the other samples and standards. The results achieved for the stability samples were in agreement with those obtained for the freshly prepared QC samples; i.e. a positive bias was observed in all but one case (Table 1).

TABLE 1

Linearity, QC, and Sample Stability Results for the Carbowax/Templated Resin Fiber and $C_{18}$ Fiber*

| | CW/TPR Fiber | | | | | $C_{18}$ Fiber | | | | |
|---|---|---|---|---|---|---|---|---|---|---|
| | EMPA | IMPA | MMPA | PMPA | CMPA | EMPA | IMPA | MMPA | PMPA | CMPA |
| $R^2$ | 0.9999 | 0.9996 | 0.9996 | 0.9999 | 0.9999 | 0.9991 | 0.9998 | 0.9999 | 0.9994 | 0.9999 |
| S/N of 1 ng/mL Standard | 7:1 | 10:1 | 14:1 | 28:1 | 41:1 | 2:1 | 11:1 | 20:1 | 166:1 | 90:1 |
| | Reported Concentrations (ng/mL) | | | | | Reported Concentrations (ng/mL) | | | | |
| QCL (15) | 41.7 | 38.1 | 32.4 | 21.6 | 23.2 | 20.9 | 21.6 | 23.4 | 24.0 | 23.4 |
| QCH (75) | 97.1 | 95.1 | 90.4 | 84.9 | 84.7 | 75.5 | 78.6 | 79.5 | 83.9 | 78.7 |
| QCL Stability | 21.1 | 15.9 | 15.4 | 13.4 | 17.0 | 27.0 | 31.9 | 34.9 | 42.2 | 34.5 |
| QCH Stability | 95.1 | 79.4 | 62.2 | 71.7 | 76.5 | 77.4 | 85.9 | 86.4 | 92.0 | 96.7 |

We claim:

1. A method of collecting, from a liquid sample, a degradation product of an organophosphonate nerve agent, which consists of
   adjusting the pH of the liquid sample to below about 3 with an acid having a pKa lower than 5;
   adding a known amount of an isotopically labeled alkyl methylphosphonic acid to the liquid sample; and
   performing solid phase microextraction by contacting the liquid sample having a pH below about 3 and the isotopically labeled alkyl methylphosphonic acid added thereto with a solid phase microextraction (SPME) fiber for a given period.

2. The method of claim 1, wherein the given period is less than about 15 minutes.

3. The method of claim 1, wherein the given period is about 1 minute to about 10 minutes.

4. A method of analyzing a degradation product of an organophosphonate nerve agent having been collected from a liquid sample by a collection method consisting of adjusting the pH of the liquid sample to below about 3 with an acid having a pKa lower than 5, adding a known amount of an isotopically labeled alkyl methylphosphonic acid to the liquid sample, and performing solid phase microextraction by contacting the liquid sample having a pH below about 3 and the isotopically labeled alkyl methylphosphonic acid added thereto with a solid phase microextraction (SPME) fiber, which said analyzing comprises
   desorbing the degradation product from the SPME fiber after having been adsorbed thereon and stored for a given period; and
   assaying the desorbed degradation product.

5. The method of claim 4, wherein the desorbed degradation product is assayed using nuclear magnetic resonance, chromatography, mass spectrometry, or a combination thereof.

6. The method of claim 4, wherein the desorbed degradation product is assayed using gas-chromatography-mass spectrometry (GC/MS), liquid chromatography-tandem mass spectrometry (LC/MS/MS), or high-performance liquid chromatography (HPLC).

7. The method of claim 4, wherein the given period is greater than 3 months.

8. The method of claim 4, wherein the given period is greater than 5 months.

9. The method of claim 1, wherein the method is performed using a kit comprising
   a solid phase microextraction (SPME) fiber;
   a volumetric container;
   an acid having a pKa lower than 5; and
   an internal standard solution comprising a known amount of an isotopically labeled alkyl methylphosphonic acid.

10. The method of claim 9, wherein the acid is acetic acid, formic acid, methane sulfonic acid, phosphoric acid, sulfuric acid, hydrochloric acid, hydrobromic acid, hydroiodic acid, trifluoromethane sulfonic acid, or toluenesulfonic acid.

11. The method of claim 9, wherein the acid is provided in an amount of 50 µL to 3 mL.

12. The method of claim 9, wherein the isotopically labeled alkyl methylphosphonic acid is present in a concentration of 100 ng/mL to 1 µl/mL.

13. The method of claim 9, wherein the isotopically labeled alkyl methylphosphonic acid is pinacolyl methylphosphonic acid (PMPA), 2-(methyl)propyl methylphosphonic acid (MMPA), cyclohexyl methylphosphonic acid (CMPA), isopropyl methylphosphonic acid (IMPA), ethyl methylphosphonic acid (EMPA), or a combination of one or more thereof.

14. The method of claim 9, wherein the SPME fiber comprises polydimethylsiloxane (PDMS), divinylbenzene (DVB), polyethylene glycol (PEG), octadecylsilyl ($C_{18}$), polyacrylate (PA), or a combination of one or more thereof.

15. The method of claim 9, wherein the SPME fiber comprises a polyethylene glycol templated resin (CW/TPR) or octadecylsilyl ($C_{18}$).

16. The method of claim 9, wherein the SPME fiber is provided as a retractable fiber assembly.

17. The method of claim 9, wherein the SPME fiber is provided as a coating on the volumetric container.

18. The method of claim 9, wherein the SPME fiber is attached to a cap for the volumetric container.

19. The method of claim 9, wherein the acid is acetic acid, formic acid, methane sulfonic acid, phosphoric acid, sulfuric acid, hydrochloric acid, hydrobromic acid, hydroiodic acid, trifluoromethane sulfonic acid, or toluenesulfonic acid;

the isotopically labeled alkyl methylphosphonic acid is pinacolyl methylphosphonic acid (PMPA), 2-(methyl) propyl methylphosphonic acid (MMPA), cyclohexyl methylphosphonic acid (CMPA), isopropyl methylphosphonic acid (IMPA), ethyl methylphosphonic acid (EMPA), or a combination of one or more thereof and is present in a concentration of 100 ng/mL to 1 μl/mL; and the SPME fiber comprises polydimethylsiloxane (PDMS), divinylbenzene (DVB), polyethylene glycol (PEG), octadecylsilyl ($C_{18}$), polyacrylate (PA), or a combination of one or more thereof.

* * * * *